United States Patent
Lin

(10) Patent No.: US 8,165,643 B2
(45) Date of Patent: Apr. 24, 2012

(54) CHARGING CRADLE

(75) Inventor: Chu-Keng Lin, Taipei (TW)

(73) Assignee: Cheng Uei Precision Industry Co., Ltd., New Taipei (TW)

( * ) Notice: Subject to any disclaimer, the term of this patent is extended or adjusted under 35 U.S.C. 154(b) by 503 days.

(21) Appl. No.: 12/510,268

(22) Filed: Jul. 28, 2009

(65) Prior Publication Data

US 2011/0028189 A1 Feb. 3, 2011

(51) Int. Cl.
*H04M 1/00* (2006.01)
*H02J 7/00* (2006.01)

(52) U.S. Cl. .................. 455/573; 455/572; 320/115

(58) Field of Classification Search .............. 455/572, 455/573, 569.1; 320/115
See application file for complete search history.

(56) References Cited

U.S. PATENT DOCUMENTS

| | | | |
|---|---|---|---|
| 5,691,618 A * | 11/1997 | Kobayashi et al. | 320/115 |
| 5,946,637 A * | 8/1999 | Umbach et al. | 455/573 |
| D592,132 S * | 5/2009 | Lin et al. | D13/107 |
| D601,089 S * | 9/2009 | Lin | D13/108 |
| 7,697,963 B1 * | 4/2010 | Pomery | 455/572 |
| 7,923,964 B2 * | 4/2011 | Lin et al. | 320/115 |
| 2002/0115480 A1 * | 8/2002 | Huang | 455/573 |

* cited by examiner

*Primary Examiner* — Duc M Nguyen
(74) *Attorney, Agent, or Firm* — Lin & Associates IP, Inc.

(57) ABSTRACT

A charging cradle has a rectangular cradle body defined an upper surface, a front surface and two opposite lateral surfaces thereon. An end of the upper surface adjacent to the front surface is formed with a subjacent surface lower than the upper surface and connecting with the upper surface by a first inclined surface. The upper surface has a receiving chamber extending along a front and rear direction. A charging base having a rotation portion defined a rectangular base mounted in the receiving chamber and rotatable around an axis perpendicular to the two lateral surfaces. A rear end of the rectangular base is extended downwards to form a receiving portion. Two opposite sides of the rectangular base have portions adjacent to a front end thereof extended laterally to form resisting portions, free ends of which extend downwards to form holding plates located at two opposite sides of the cradle body.

11 Claims, 5 Drawing Sheets

CHARGING CRADLE

BACKGROUND OF THE INVENTION

1. Field of the Invention

The present invention relates to a charging cradle, and more particularly to a charging cradle for a mobile phone.

2. The Related Art

A conventional charging cradle includes a rectangular cradle body and a charging base rotatably mounted on the cradle body. The cradle body has a receiving chamber at an upper surface thereof for receiving the charging base. The charging base has an approximately rectangular base with a shape capable of mating with the shape of the receiving chamber. The base has an end extended downwards and perpendicularly to form a receiving portion for receiving an output connector. When the charging cradle is in the closed state, the receiving portion and the base are received into the receiving chamber. When the charging cradle is in the open state for charging up a mobile phone, the receiving portion resists against a front inner wall of the receiving chamber and the output connector and the base are exposed out of the receiving chamber. Afterwards, the charging connector of the mobile phone will be connected with the output connector of the charging cradle, with a bottom surface and an end of the mobile phone depending on and resisting against the base and the upper surface of the cradle body, respectively.

Nevertheless, when the mobile phone is charged by the conventional charging cradle, the mobile phone will depend on the base with the bottom thereof resisting against the upper surface of the cradle body, which makes a contacting area between the mobile phone and the charging cradle narrowed. Thus it is easy to produce a shake between the mobile phone and the charging base and make the connection of the mobile phone and the charging cradle unstable.

SUMMARY OF THE INVENTION

Accordingly, an object of the present invention is to provide a charging cradle capable of charging a mobile phone. The charging cradle has a rectangular cradle body defining an upper surface, a front surface intersecting with the upper surface, and two opposite lateral surfaces respectively connecting with the upper surface and the front surface. An end of the upper surface adjacent to the front surface is formed with a subjacent surface lower than the upper surface and connecting with the upper surface by a first inclined surface. The upper surface has a receiving chamber extending along a front and rear direction, and passing through the first inclined surface and the subjacent surface. A charging base has a rotation portion. The rotation portion defines a rectangular base mounted in the receiving chamber and rotatable around an axis perpendicular to the two lateral surfaces. A rear end of the rectangular base is extended downwards to form a receiving portion which is received into the receiving chamber in a closed state. Two opposite sides of the rectangular base have portions adjacent to a front end thereof extended laterally to form resisting portions laying above the subjacent surface in the closed state. Free ends of the resisting portion extend downwards to form holding plates located at two opposite sides of the cradle body. The receiving portion has a front portion rotated to abut a front wall of the receiving chamber for keeping oblique state of the rotation portion in an open state. A substantially middle portion of the rectangular base is turned to lean against the first inclined surface in the open state for supporting the inserted mobile phone between the holding plates.

As described above, when the charging cradle is in the open state to receive the mobile phone, the substantially middle portion of the rectangular base will lean against the first inclined surface to enlarge the contacting area between the mobile phone and the charging cradle, for supporting the inserted mobile phone between the holding plates, which makes the charging cradle and the mobile phone connected steadily. So the charging cradle is excellent and can be used widely.

BRIEF DESCRIPTION OF THE DRAWINGS

The present invention will be apparent to those skilled in the art by reading the following description of an embodiment thereof, with reference to the attached drawings, in which.

DETAILED DESCRIPTION OF THE PREFERRED EMBODIMENT

Figure 1:
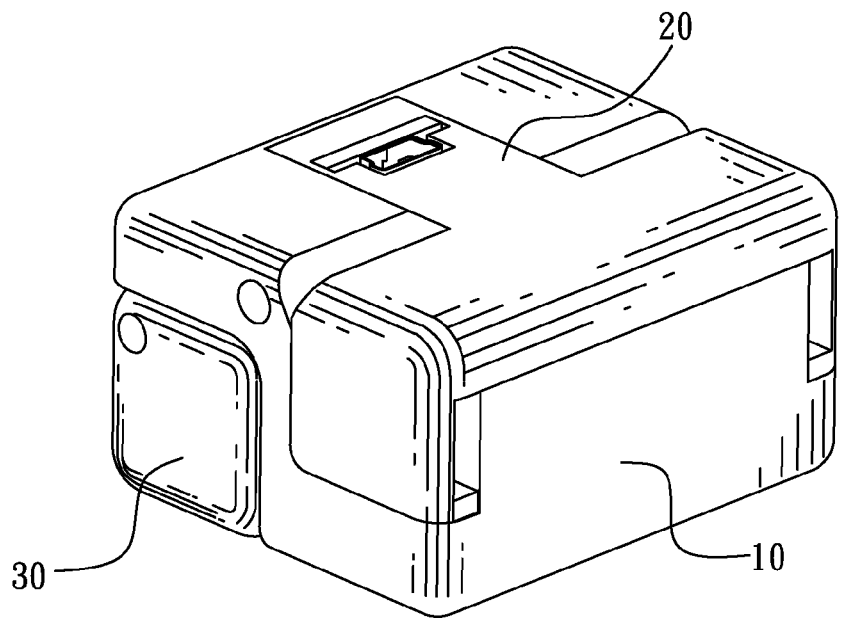
FIG. 1 is a perspective view of a charging cradle according to the present invention.
Figure 2:
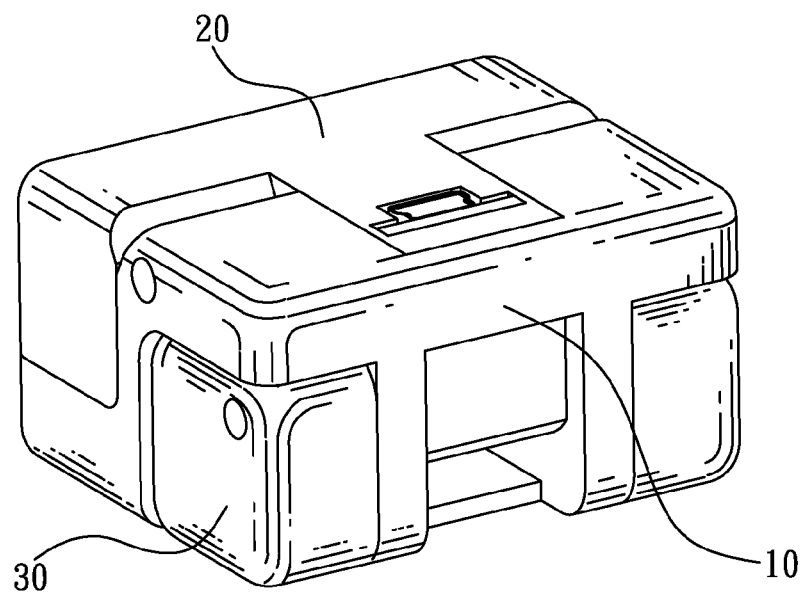
FIG. 2 is a perspective view of the charging cradle shown in FIG. 1 seen from another direction.

With reference to FIG. 1 and FIG. 2, a charging cradle according to the present invention includes a rectangular cradle body 10, a charging base 20 rotatably mounted on the cradle body 10 and two casings 30 pivotedly coupled with the cradle body 10.

Figure 3:
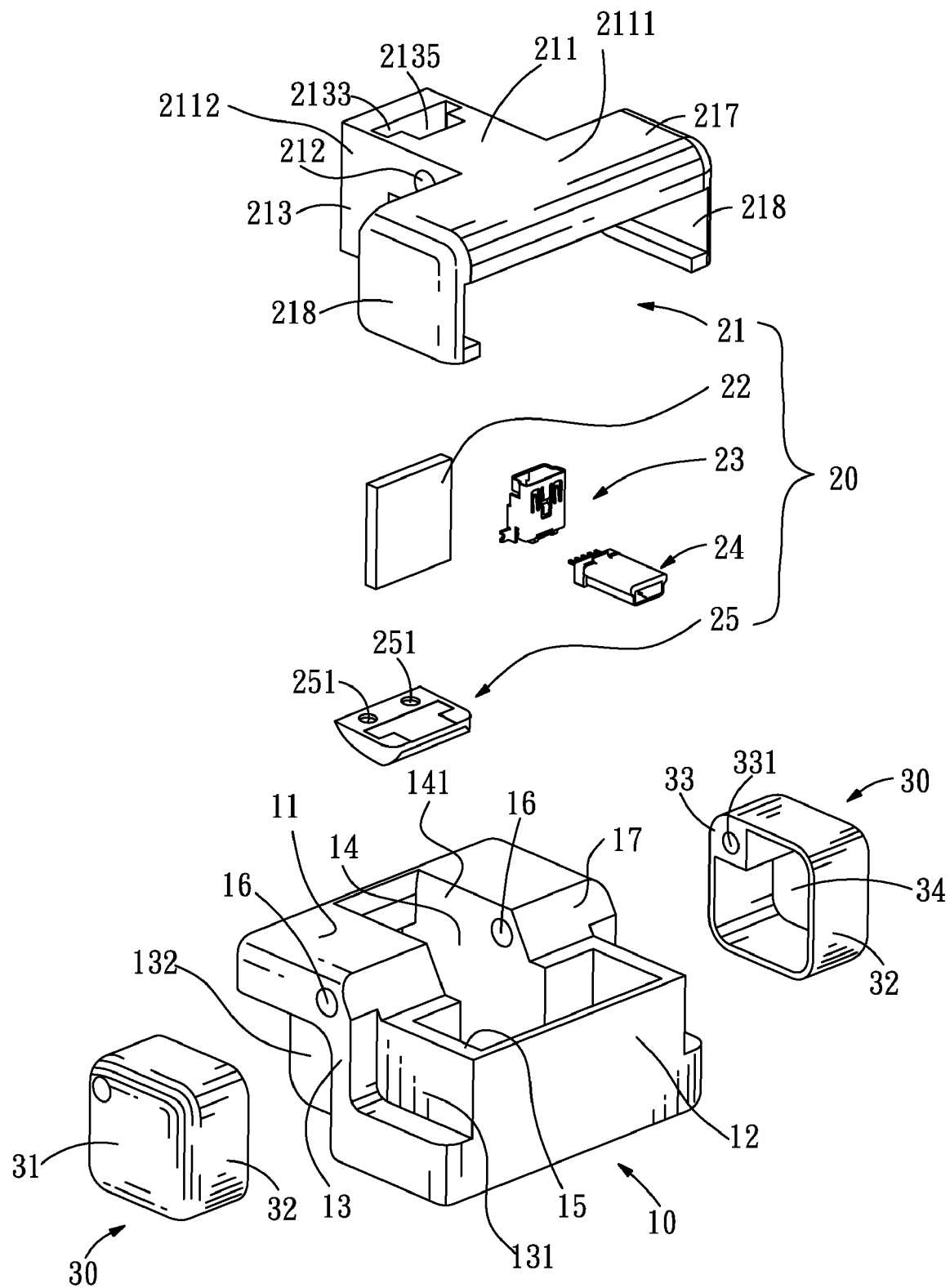
FIG. 3 is an exploded view of the charging cradle shown in FIG. 1.
Figure 4:
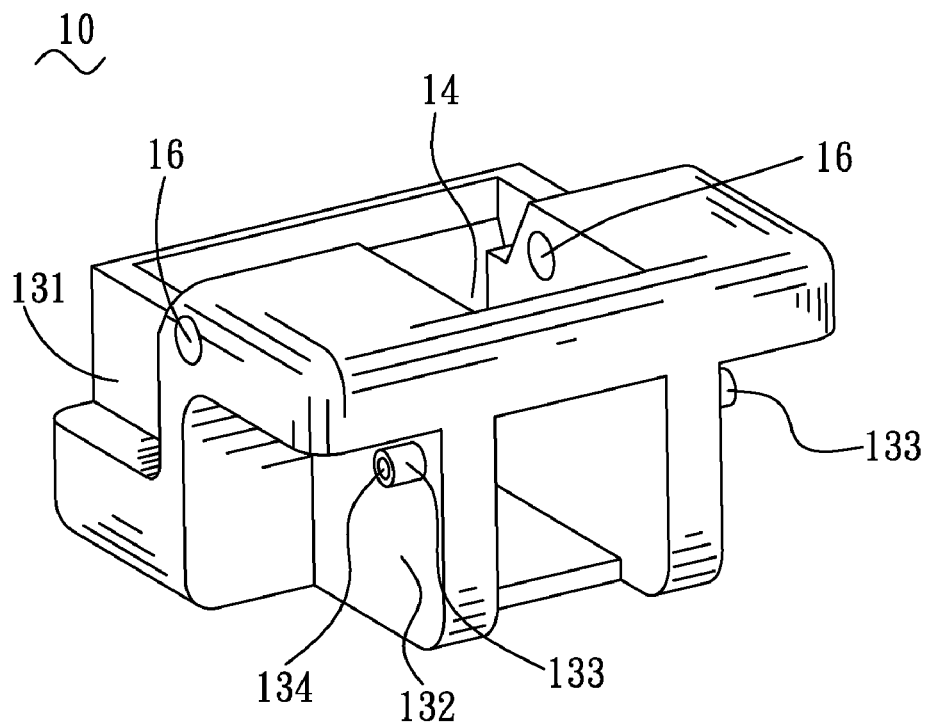
FIG. 4 is a perspective view of a cradle body of the charging cradle shown in FIG. 3.
Figure 5:
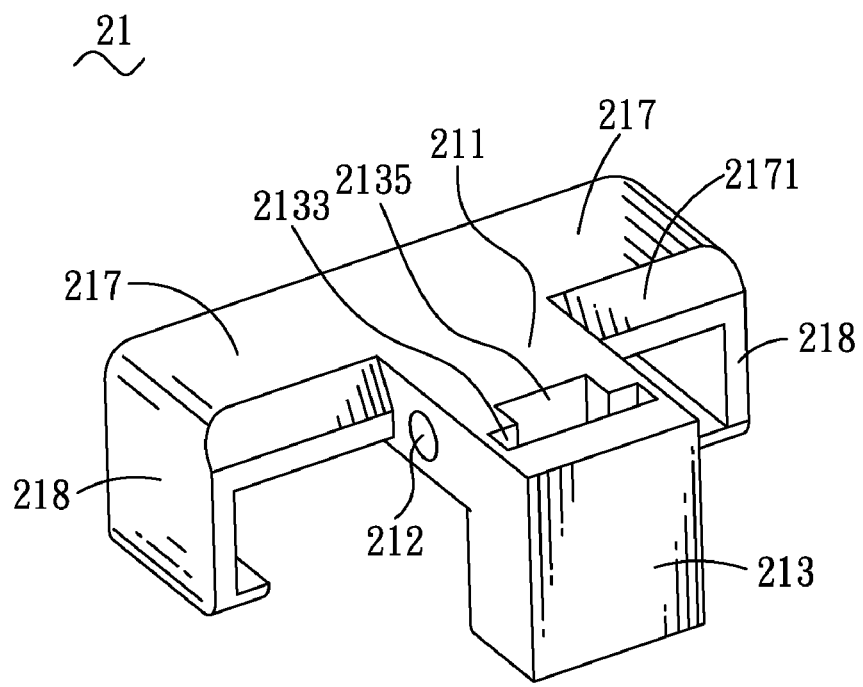
FIG. 5 is a perspective view of a charging base of the charging cradle shown in FIG. 3.
Figure 6:
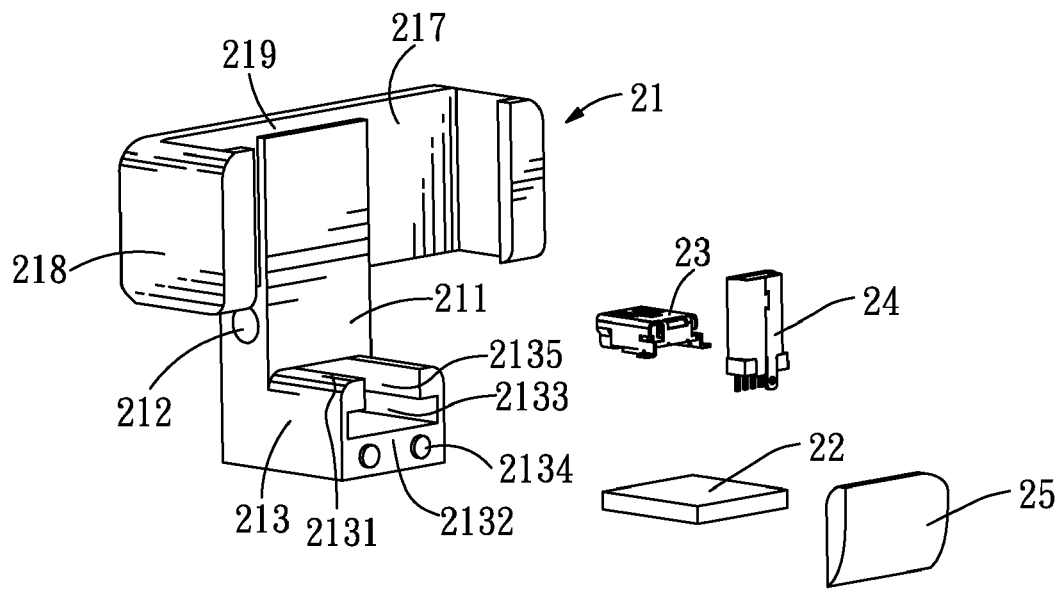
FIG. 6 is an exploded view of the charging base of the charging cradle shown in FIG. 3.
Figure 7:
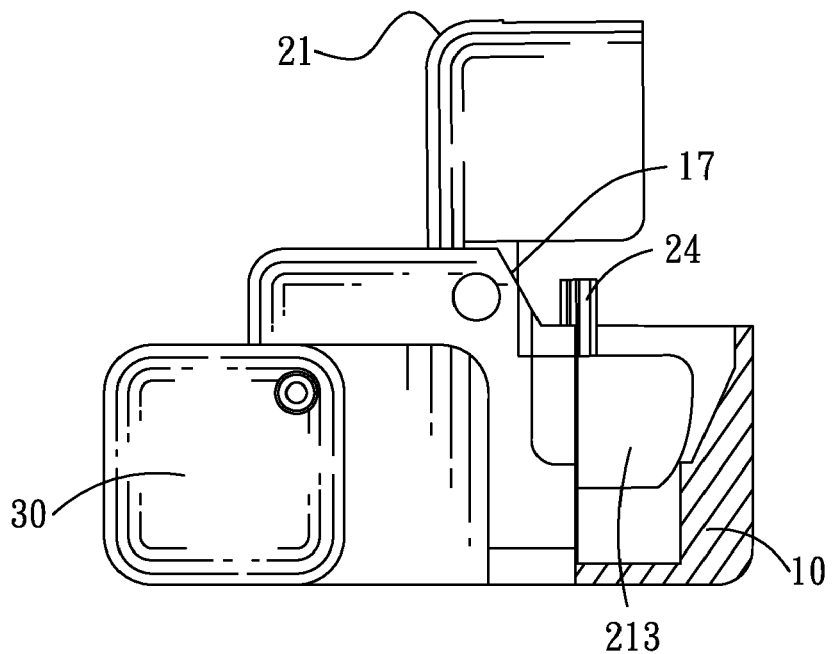
FIG. 7 is a lateral view showing a state that the charging cradle shown in FIG. 1 is separated with a mobile phone, in order to show the inner structure clearly, the cradle body shows a partly cross-sectional view.
Figure 8:
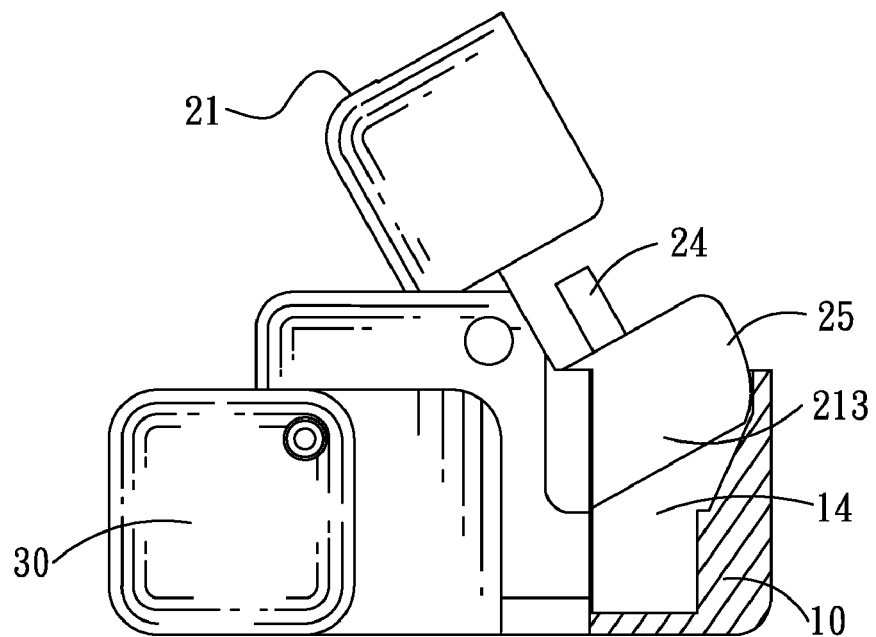
FIG. 8 is a lateral view of the charging cradle shown in FIG. 1, wherein the charging cradle is in an open state, in order to show the inner structure clearly, the cradle body shows a partly cross-sectional view.
Figure 9:
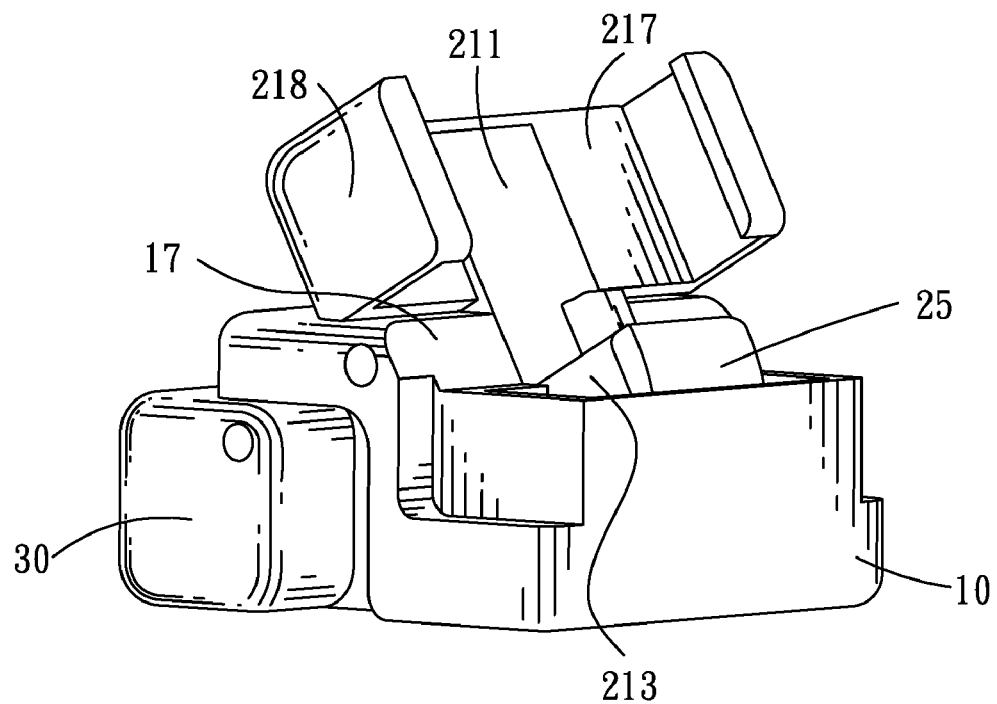
FIG. 9 is a perspective view of the charging cradle shown in FIG. 1, wherein the charging cradle is in the open state and a casing of the charging cradle shown in FIG. 1 is unfolded.

Please refer to FIG. 3 and FIG. 4, the cradle body 10 defines an upper surface 11, a front surface 12 and two opposite lateral surfaces 13. The upper surface 11 has a front portion concaved downwards to form a subjacent surface 15 which is lower than the upper surface 11. The upper surface 11 and the subjacent surface 15 are connected by a first inclined surface 17. The upper surface 11 further has a rectangular receiving chamber 14 at a middle portion thereof extending frontward and rearward and passing through the subjacent surface 15 and the first inclined surface 17. The receiving chamber 14 has two opposite inner walls 141. Each of the inner walls 141 is formed with an axis hole 16 thereon. The lateral surface 13 of the cradle body 10 is provided with a gap 131 located at a front portion thereof and extended to the front surface 12 and the subjacent surface 15, and a receiving recess 132 located at a rear portion thereof and extended to a bottom surface and a rear surface of the cradle body 10. Herein, the receiving recess 132 is spaced away from the gap 131. A bottom of the receiving recess 132 protrudes outwards to form a column pivot 133 with a fixing hole 134 formed thereon. In this embodiment, the pivot 133 is adjacent to the upper surface 11 and the rear surface of the cradle body 10.

Please refer to FIGS. 3-9, the charging base 20 has a rotation portion 21, a circuit board 22, an input connector 23 levelly mounted on the circuit board 22, an output connector 24 perpendicularly fixed on the circuit board 22 and a buckling portion 25.

The rotation portion 21 has an approximately rectangular base 211 corresponding to the receiving chamber 14 of the cradle body 10, and a rectangular resisting portion 217 intersecting with the base 211 by a middle portion of a long side thereof connecting with one end of the base 211 to show as a T shape. The base 211 has two opposite lateral surfaces 2112 formed with two mounting holes 212 communicated with each other and corresponding to the axis holes 16 of the cradle body 10. The other end of the base 211 is perpendicularly extended downwards to form a receiving portion 213. The receiving portion 213 has an inner surface 2131 opposite to a rear wall of the receiving chamber 14 in a closed state and a bottom surface 2132 perpendicular to the inner surface 2131. The bottom surface 2132 defines a first recess 2133 at a middle portion thereof reaching to a top surface 2111 of the base 211 for receiving the circuit board 22, and two protrusions 2134 adjacent to the first recess 2133. The inner surface 2132 has a second recess 2135 communicating with and narrower than the first recess 2133 and reaching to the top surface 2111 of the base 211, for receiving the input connector 23 and the output connector 24. The output connector 24 protrudes out of the second recess 2135. Two ends of the resisting portion 217 extend downwards to form two holding plates 218. The holding plates 218 are L-shape and have oriented ends facing each other, locating in the gaps 131 of the cradle body 10. A side of the resisting portion 217 adjacent to the receiving portion 213 is provided with a second inclined surface 2171. The buckling portion 25 has a surface defined two fixing holes 251 thereon. The two protrusions 2134 of the bottom surface 2132 is engaged with the fixing holes 251 to fix the buckling portion 25 on the bottom surface 2132 of the receiving portion 213, for preventing the circuit board 22 and the input connector 23 from falling off the corresponding first and second recesses 2133, 2135.

The casing 30 has a rectangular board 31. The board 31 has four sides extended perpendicular to form four connecting walls 32 connected with each other to form a rectangular recess 34 thereamong. A protrusion 33 is located at a corner of the recess 34. The protrusion 33 is provided with an inserting hole 331 thereon passing through the board 31 corresponding to the pivot 133 of the cradle body 10.

When in assembly, the base 211 and the receiving portion 213 are received into the receiving chamber 14. The holding plate 218 stands against a side of the gap 131 and the resisting portion 217 locates above the subjacent surface 15. A connecting element (not shown) passes through the axis holes 16 and the mounting holes 212 to make the charging base 20 rotatably mount on the cradle body 10. The casing 30 is pivoted to the receiving recess 132, by the column pivot 133 being engaged with the inserting hole 331. A rivet (not shown) passes through the fixing hole 134 and the inserting hole 331, with an end thereof resisting against the board 31 to prevent the casing 30 taking off the cradle body 10. At this time, the charging cradle is in the closed state.

When the charging cradle is used to charge a mobile phone with charging connector provided in an end thereof, firstly need to open the charging cradle. The charging base 20 is rotated until the buckling portion 25 on the bottom surface 2132 of the receiving portion 213 abuts an upper portion of a front wall of the receiving chamber 14. Herein, the holding plate 218 leaves away from the gap 131, the second inclined surface 2171 of the resisting portion 217 is seated on the upper surface 11 of the cradle body 10 and a substantially middle portion of the rectangular base 211 leans against the first inclined surface 17, which makes the charging base 20 stay in the open state steadily to support the mobile phone. After that, the mobile phone is inserted between the two holding plates 218, along an inclined direction of the first inclined surface 17, until the charging connector thereof is connected with the output connector 24 of the charging cradle. For preventing the mobile phone from being discharged on account of toppling, the casing 30 is rotated to locate rearward of a rear surface of the cradle body 10. The output connector 24 is able to be pulled and pushed along the second recess 2135, which makes the space between the output connector 24 and the base 211 adjust to adapt the mobile phone of different thickness.

When the mobile phone is completely charged, the mobile phone is pressed downwards along the inclined direction of the first inclined surface 17, which makes the rotation portion 21 turn and the receiving portion 213 move into the receiving chamber 14. When the base 211 of the rotation portion 21 is vertical with respect to the subjacent surface 15, the rotation portion 21 will stop turning. At this time, the end of the mobile phone rests against the subjacent surface 15, the output connector 24 and the charging connector of the mobile phone are separated. So the mobile phone can be easily taken out of the charging cradle. The whole removal operation can be finished only by one hand.

As described above, when the charging cradle is in the open state, the buckling portion 25 on the bottom surface 2132 of the receiving portion 213 restrains against the upper portion of the front wall of the receiving chamber 14, the second inclined surface 2171 of the resisting portion 217 is seated on the upper surface 11 of the cradle body 10, which makes the charging base 20 stay in the open state steadily to receive the mobile phone. A substantially middle portion of the rectangular base 211 will lean against the first inclined surface 17 to enlarge the contacting area between the mobile phone and the charging cradle, for supporting the inserted mobile phone between the holding plates 218, which makes the charging cradle and the mobile phone connect steadily.

The foregoing description of the present invention has been presented for purposes of illustration and description. It is not intended to be exhaustive or to limit the invention to the precise form disclosed, and obviously many modifications and variations are possible in light of the above teaching. Such modifications and variations that may be apparent to those skilled in the art are intended to be included within the scope of this invention as defined by the accompanying claims.

What is claimed is:

1. A charging cradle for charging a mobile phone, comprising:
   a rectangular cradle body defining an upper surface, a front surface intersecting with the upper surface, and two opposite lateral surfaces respectively connecting with the upper surface and the front surface, an end of the upper surface adjacent to the front surface formed with a subjacent surface lower than the upper surface and connecting with the upper surface by a first inclined surface, the upper surface having a receiving chamber extending along a front and rear direction, and passing through the first inclined surface and the subjacent surface; and
   a charging base having a rotation portion, the rotation portion defining a rectangular base mounted in the receiving chamber and rotatable around an axis perpendicular to the two lateral surfaces, a rear end of the rectangular base extending downwards to form a receiving portion which is received in the receiving chamber in a closed state, two opposite sides of the rectangular base having portions adjacent to a front end thereof extending laterally to form resisting portions laying above the subjacent surface in the closed state, free ends of the resisting portions extend downwards to form holding plates located at two opposite sides of the cradle body, wherein the receiving portion has a front portion rotated to abut a front wall of the receiving chamber for keeping oblique state of the rotation portion in an open state, a substantially middle portion of the rectangular base is turned to lean against the first inclined surface in the open state for supporting the inserted mobile phone between the holding plates.

2. The charging cradle as claimed in claim 1, wherein each of the two opposite lateral surfaces has a receiving recess, the charging cradle has two casings pivoted to the receiving recesses respectively, the casings are rotated to locate rearward of a rear surface of the cradle body for preventing the cradle body from toppling when the mobile phone is charged.

3. The charging cradle as claimed in claim 1, wherein a side of the resisting portion adjacent to the receiving portion defines a second inclined surface which is seated on the upper surface of the cradle body in the open state.

4. The charging cradle as claimed in claim 1, wherein each of the lateral surfaces has a gap at a front portion thereof and reaching to the subjacent surface and the front surface, the holding plate is received in the gap in the closed state.

5. The charging cradle as claimed in claim 4, wherein each of the lateral surfaces has a receiving recess at a rear portion and reaching to a bottom surface and a rear surface of the cradle body, the receiving recess is spaced from the gap for receiving a casing.

6. The charging cradle as claimed in claim 5, wherein a bottom of the receiving recess is protruded outwards to form a column pivot adjacent to a rear and upper portion thereof, with a fixing hole formed thereon, the casing has an inserting hole at a corner thereof for engaging with the pivot of the cradle body.

7. The charging cradle as claimed in claim 6, wherein the casing has a rectangular board, and four connecting walls extended perpendicularly from four sides of the board and connected with each other, forming a rectangular recess thereamong, a protrusion is located at a corner of the recess, the inserting hole is formed on the protrusion.

8. The charging cradle as claimed in claim 1, wherein the two holding plates are L-shape and have oriented ends facing each other, each of the oriented ends stands against a side of the gap in the closed state.

9. The charging cradle as claimed in claim 1, wherein the receiving portion of the charging base has an inner surface opposite to a rear wall of the receiving chamber in the closed state, and a bottom surface perpendicular to the inner surface, the bottom surface defines a first recess at a middle portion thereof, reaching a top surface of the base, for receiving a circuit board, the inner surface has a second recess reaching the top surface of the base, the second recess communicates with and is narrower than the first recess, for receiving an input connector and an output connector.

10. The charging cradle as claimed in claim 9, wherein a buckling portion is coupled with the bottom surface of the receiving portion, preventing the circuit board and the input connector falling from the corresponding first and second recesses.

11. The charging cradle as claimed in claim 10, wherein the bottom surface of the receiving portion has protrusions adjacent to the first recess, a buckling portion has fixing holes engaging with the protrusions.

\* \* \* \* \*